(12) United States Patent
Kawabata et al.

(10) Patent No.: US 8,207,359 B2
(45) Date of Patent: Jun. 26, 2012

(54) METHOD FOR PRODUCING EPOXY COMPOUND

(75) Inventors: Tomonori Kawabata, Toyonaka (JP); Hiroaki Abekawa, Toyonaka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 698 days.

(21) Appl. No.: 12/226,729

(22) PCT Filed: Apr. 26, 2007

(86) PCT No.: PCT/JP2007/059434
§ 371 (c)(1),
(2), (4) Date: Feb. 19, 2009

(87) PCT Pub. No.: WO2007/126139
PCT Pub. Date: Nov. 8, 2007

(65) Prior Publication Data
US 2009/0209772 A1 Aug. 20, 2009

(30) Foreign Application Priority Data
Apr. 27, 2006 (JP) ............................... P2006-123127

(51) Int. Cl.
*C07D 301/12* (2006.01)
*C07D 301/06* (2006.01)
(52) U.S. Cl. ...................................... 549/533; 549/531
(58) Field of Classification Search .................. 549/531, 549/533
See application file for complete search history.

(56) References Cited

U.S. PATENT DOCUMENTS

| 5,221,795 A | 6/1993 | Clerici et al. |
| 5,252,758 A | 10/1993 | Clerici et al. |
| 6,008,386 A | 12/1999 | Dessu et al. |

FOREIGN PATENT DOCUMENTS

| EP | 0878470 A | 11/1998 |
| GB | 1209321 A | 10/1970 |
| JP | 04-352771 A | 12/1992 |
| JP | 10-228681 A | 12/1998 |
| JP | 10338681 | * 12/1998 |
| JP | 2002-511455 | 4/2002 |

OTHER PUBLICATIONS

Meiers et al., "Synthesis of propylene oxide from propylene, oxygen, and hydrogen catalyzed by palladium-platinum-containing titanium silicalite," *Journal of Catalysis*, 1998, vol. 176, No. 2, pp. 376-386.
Meirs et al , Synthesis of Propylene Oxide from Propylene, Oxygen, and Hydrogen Catalyzed by Pallaau-Platinum—Containing Titanium Silicalite, Journal of Catalysis, 176:376-386 (1998).

* cited by examiner

*Primary Examiner* — Taylor Victor Oh
(74) *Attorney, Agent, or Firm* — Fitch, Even, Tabin & Flannery, LLP

(57) ABSTRACT

A method for producing an epoxy compound characterized by comprising contacting an olefin, oxygen and hydrogen with a noble metal and a crystalline titanosilicate having an MFI structure in a liquid phase in the presence of a quinoid compound selected from the group consisting of a phenanthraquinone compound and a compound represented by formula (1)

[Formula 1]

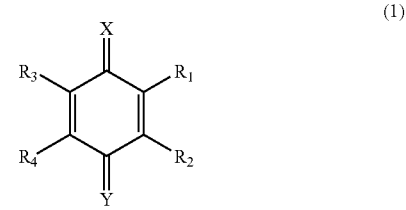

(1)

wherein $R_1$, $R_2$, $R_3$ and $R_4$ represent a hydrogen atom, or $R_1$ and $R_2$ or $R_3$ and $R_4$ adjacent to each other are each independently bound at the ends and represent, together with a carbon atom of a quinone to which they are respectively attached, a benzene ring which may be substituted with an alkyl group or a hydroxyl group, or a naphthalene ring which may be substituted with an alkyl group or a hydroxyl group; and X and Y, which is the same or different, represent an oxygen atom or an NH group,
or a dihydro compound thereof.

12 Claims, No Drawings

METHOD FOR PRODUCING EPOXY COMPOUND

CROSS-REFERENCE TO RELATED APPLICATIONS

This is a U.S. National Phase of International Application PCT/JP2007/059434, filed Apr. 26, 2007, and claims the benefit of foreign priority under 35 U.S.C. §119 based on JP 2006-123127, filed Apr. 27, 2006, the entire disclosures of which applications are hereby incorporated herein by reference.

TECHNICAL FIELD

The present invention relates to a method for producing an epoxy compound from an olefin, oxygen and hydrogen.

BACKGROUND ART

As a method for producing an epoxy compound from an olefin, oxygen and hydrogen, for example, a method using a noble metal compound and a titanosilicate is known.

As a method for producing propylene oxide using a catalyst containing TS-1 and Pd, a method using water as a solvent for reaction for producing propylene oxide from hydrogen, oxygen and propylene in the presence of a catalyst which supports Pd and Au on TS-1 and adding hydroquinone has been reported (See Heisei 13 nen-do Jisedai Kagaku Process Gijutsu Kaihatsu and Non-halogen Kagaku Process Gijutsu Kaihatsu Seika Houkokusho (Achievement Report for the Year 2001 of Next-generation Chemical Process Technical Development and Non-halogen Chemical Process Technical Development), 249-258 (2002)). In the meantime, it has been reported that when a mixed solvent of water and methanol is used in a reaction for producing propylene oxide from hydrogen, oxygen and propylene using palladium and TS-1 as a catalyst and adding ammonium hydroxide, generated amount of propylene oxide increases whereas by-produced amount of propane decreases (for example, see Published Japanese translation of a PCT application No. 2002-511455). However, these methods are not necessarily satisfactory at a point of efficiency of the reaction.

DISCLOSURE OF THE INVENTION

The present invention provides a method for producing an epoxy compound from an olefin, oxygen and hydrogen effectively.

That is, the present invention relates to a method for producing an epoxy compound characterized by comprising contacting an olefin, oxygen and hydrogen with a noble metal and a crystalline titanosilicate having an MFI structure in a liquid phase in the presence of a quinoid compound selected from the group consisting of a phenanthraquinone compound and a compound represented by formula (1)

[Formula 1]

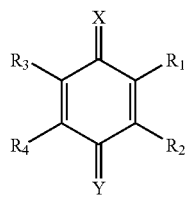

(1)

wherein $R_1$, $R_2$, $R_3$ and $R_4$ represent a hydrogen atom, or $R_1$ and $R_2$ or $R_3$ and $R_4$ adjacent to each other are each independently bound at the ends to represent, together with the carbon atoms of a quinone to which they are respectively attached, a benzene ring which may be substituted with an alkyl group or a hydroxyl group, or a naphthalene ring which may be substituted with an alkyl group or a hydroxyl group; and X and Y, which is the same or different, represent an oxygen atom or an NH group, or a dihydro compound thereof.

According to the present invention, by using a quinoid compound and a specific titanosilicate, selectivity of the epoxy compound can be improved and generated amount of a saturated hydrocarbon generated by reduction of an olefin can be suppressed, and thus, an epoxy compound can be produced more efficiently from an olefin, oxygen and hydrogen.

BEST MODE FOR CARRYING OUT THE INVENTION

Examples of the noble metal usable in the present invention include palladium, platinum, ruthenium, rhodium, iridium, osmium, gold and an alloy and a mixture thereof. Examples of preferable noble metals include palladium, platinum and gold. A more preferable noble metal is palladium.

A metal such as platinum, gold, rhodium, iridium and osmium can be added to palladium. Examples of preferable added metals include platinum.

In addition, these noble metals may be in the state of compounds such as oxides or hydroxides. They can be filled in a reaction vessel in the state of a noble metal compound as well and the part or whole thereof can be reduced under the reaction condition by hydrogen in the raw materials.

The noble metals are usually supported by a carrier and used. The noble metals can be supported by titanosilicate and used, or can be also supported by a carrier other than titanosilicate such as oxides such as silica, alumina, titania, zirconia and niobia, hydrates such as niobium acid, zirconium acid, tungstic acid and titanic acid or carbon and a mixture thereof and used. When a noble metal is supported by a carrier other than titanosilicate, the carrier supporting the noble metal can be mixed with titanosilicate and the mixture can be used as a catalyst. Among the carriers other than titanosilicate, carbon is preferable as a carrier. As a carbon carrier, active carbon, carbon black, graphite, carbon nanotube, etc. are known.

Examples of methods for preparing a noble metal supporting catalyst, include a method comprising supporting a colloidal solution of the noble metal in which noble metal particles are dispersed with a dispersant such as citric acid, polyvinyl alcohol, polyvinylpyrrolidone, sodium hexametaphosphate on a carrier by impregnation method and the like and performing calcining in an inert gas. Alternatively, such a catalyst can be prepared by supporting a noble metal compound which can be a noble metal source, for example, nitrates of noble metals such as palladium nitrate, sulfates such as palladium sulfate dihydrate, halides of noble metals such as palladium halide, carboxylate such as palladium acetate or ammine complexes such as Pd tetraammine chloride on a carrier by impregnation method and the like and then performing reduction with a reducing agent, or can be also prepared by converting a noble metal compound into a noble metal hydroxide with an alkali such as sodium hydroxide and then performing reduction with a reducing agent in a liquid phase or a gaseous phase. Examples of the reducing agent for performing reduction in a liquid phase include hydrogen, hydrazine monohydrate, formaldehyde, sodium borohydride. In the case of using hydrazine monohydrate or formaldehyde, a method of performing the procedure with addition of an alkali is also known. Examples of the reducing agent for performing reduction in a gaseous phase include hydrogen and ammonia. Preparation can be also performed by calcining and reducing a carrier which supports a noble metal source in the presence of hydrogen gas. The temperature for preferably performing reduction varies depending on the supported noble metal source but it is typically from 0° C. to 500° C. In addition, a method comprising supporting an ammine complex of noble metals such as Pd tetraammine chloride on a carrier by impregnation method and the like and performing reduction with ammonia gas generated during thermal decomposition in an inert gas can be also used. The reduction temperature varies depending on the noble metal ammine complex but when Pd tetraammine chloride is used, it is typically from 100° C. to 500° C., and preferably from 200° C. to 350° C.

In any method, the obtained catalyst can be activated by heat-treatment in an inert gas, ammonia gas, vacuum, hydrogen or air, if needed. In addition, after a compound such as an oxide or a hydroxide of a noble metal is charged in a reaction vessel and reduction can be performed under the reaction condition.

The thus obtained noble metal supporting carrier typically contains the noble metal in the range of 0.01 to 20% by weight, and preferably, 0.1 to 5% by weight.

The weight ratio of the noble metal to titanosilicate (weight of noble metal/weight of titanosilicate) is preferably 0.01 to 100% by weight, and more preferably 0.1 to 20% by weight.

The crystalline titanosilicate having an MFI structure usable in the present invention means a crystalline titanosilicate having an MFI structure by Framework Type Code of IZA (International Zeolite Association) and examples thereof include specifically TS-1.

The titanosilicate is a general term representing an entity in which a part of Si of a porous silicate ($SiO_2$) is replaced by Ti. Ti of titanosilicate is within the $SiO_2$ framework, and the fact that Ti is contained within the $SiO_2$ skeleton can be easily confirmed by the presence of a peak at 210 nm to 230 nm in ultraviolet-visible absorption spectrum. In addition, Ti of $TiO_2$ is usually 6-coordinate but Ti of titanosilicate is 4-coordinate, and therefore it can be confirmed easily by measuring a coordination number by titanium K-edge XAFS analysis, etc.

The general method for synthesizing these titanosilicates is a method using a surfactant as a template or a structure directing agent and comprising hydrolyzing a titanium compound and a silicon compound, crystallizing or improving pore regularity by hydrothermal synthesis method and the like as required, and then removing the surfactant by calcining or extraction.

As a quinoid compound, compounds of the following formula (1) and phenanthraquinone compounds are exemplified,

[Formula 1]

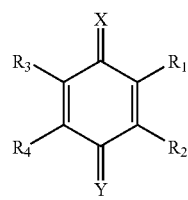

(1)

wherein $R_1$, $R_2$, $R_3$ and $R_4$ represent a hydrogen atom, or $R_1$ and $R_2$ or $R_3$ and $R_4$ adjacent to each other are each independently bound at the ends to represent, together with the carbon atoms of a quinone to which they are respectively attached, a benzene ring which may be substituted with an alkyl group or a hydroxyl group, or a naphthalene ring which may be substituted with an alkyl group or a hydroxyl group; and X and Y, which is the same or different, represent an oxygen atom or an NH group.

1) Benzoquinone (1A) of formula (1) in which $R_1$, $R_2$, $R_3$ and $R_4$ are a hydrogen atom and both of X and Y are an oxygen atom;

2) Quinonimine compound (1B) of formula (1) in which $R_1$, $R_2$, $R_3$ and $R_4$ are a hydrogen atom, and X is an oxygen atom and Y is an NH group; and 3) Quinonediimine compound (1C) of formula (1) in which $R_1$, $R_2$, $R_3$ and $R_4$ are a hydrogen atom and X and Y are an NH group can be exemplified.

The quinoid compound of formula (1) includes the following compound represented by Formula (2):

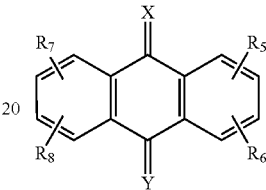

wherein X and Y, which are the same or different, represent an oxygen atom or an NH group; and $R_5$, $R_6$, $R_7$ and $R_8$, which are the same or different, represent a hydrogen atom, a hydroxyl group or an alkyl group, for example, a $C_1$-$C_5$ alkyl group such as methyl, ethyl, propyl, butyl and pentyl.

Preferably, X and Y represent an oxygen atom in formulas (1) and (2). The quinoid compound of formula (1) in which X and Y are oxygen atoms is called as a quinone compound or p-quinone compound in particular, and further, the quinoid compound of formula (2) in which X and Y are oxygen atoms is called as an anthraquinone compound in particular.

Examples of the phenanthraquinone compound include 1,2-, 1,4-, 3,4- and 9,10-phenanthraquinone.

Compounds of the following formulas (3) and (4) which are dihydro compounds of the compound of the above formulas (1) and (2) are exemplified, Formula (3)

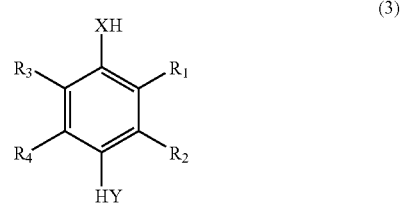

(3)

wherein $R_1$, $R_2$, $R_3$ and $R_4$ and X and Y are the same as defined in the above formula (1), Formula (4)

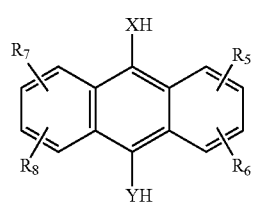

(4)

wherein X, Y, and $R_5$, $R_6$, $R_7$ and $R_8$ are the same as defined in the above formula (2).

Preferably, X and Y represent an oxygen atom in formulas (3) and (4). The dihydro compound of the quinoid compound of formula (3) in which X and Y are oxygen atoms are called as a dihydroquinone compound or dihydro ρ-quinone compound in particular, and further, the dihydro compound of the quinoid compound of formula (4) in which X and Y are oxygen atoms are called a dihydroanthraquinone compound in particular.

Specific examples of the quinone compound include benzoquinone, naphthoquinone and anthraquinone, for example, 2-alkylanthraquinone compounds such as 2-ethylanthraquinone, 2-t-butylanthraquinone, 2-amylanthraquinone, 2-methylanthraquinone, 2-butylanthraquinone, 2-t-amylanthraquinone, 2-isopropylanthraquinone, 2-s-butylanthraquinone or 2-s-amylanthraquinone and 2-hydroxyanthraquinones, for example, polyalkylanthraquinone compounds such as 1,3-diethylanthraquinone, 2,3-dimethylanthraquinone, 1,4-dimethylanthraquinone, 2,7-dimethylanthraquinone, polyhydroxyanthraquinones such as 2,6-dihydroxyanthraquinone, naphthoquinone and mixtures thereof.

Examples of preferable quinoid compounds include anthraquinone and 2-alkylanthraquinone compounds wherein, in the formula (2), X and Y are an oxygen atom, $R_5$ is an alkyl group which substitutes at the 2-position, $R_6$ represents a hydrogen atom and $R_7$ and $R_8$ represent a hydrogen atom. Examples of preferable dihydro compounds of quinoid compounds include dihydro compounds corresponding to these preferable quinoid compounds.

Examples of methods of adding a quinoid compound or a dihydro compound of a quinoid compound (hereinbelow abbreviated as a quinoid compound derivative.) to a reaction solvent include a method of dissolving a quinoid compound derivative in a liquid phase and then using it in the reaction. For example, a hydrogenated compound of a quinoid compound such as hydroquinone and 9,10-anthracenediol may be added to a liquid phase and oxidized with oxygen in the reaction vessel and a generated quinoid compound may be used.

Examples of methods of adding a quinoid compound or a dihydro compound of a quinoid compound (hereinbelow abbreviated as a quinoid compound derivative.) to a reaction solvent also include a method of dissolving a quinoid compound derivative in a solvent and then using it in the reaction and a method of adding a hydrogenated compound of a quinoid compound such as hydroquinone to a solvent and performing oxidization with oxygen in the reaction vessel to generate a quinoid compound.

The amount of a quinoid compound derivative to be used can be typically in the range of 0.001 mmol/kg to 500 mmol/kg per unit weight of the solvent (per the weight of water and an organic solvent in total). A preferable amount of a quinoid compound is 0.01 mmol/kg to 50 mmol/kg.

Water, an organic solvent and a mixed solvent of the both can be typically used for the reaction of the present invention, and a quinoid compound derivative is dissolved therein and used. By using an organic solvent, addition of a little amount of a quinoid compound derivative enables to increase the selectivity of the epoxy compound. Examples of the organic solvent include alcohol, ketone, nitrile, ether, aliphatic hydrocarbon, aromatic hydrocarbon, halogenated hydrocarbon, ester, glycol and mixtures thereof. As a preferable organic solvent, an alcohol solvent can be included, and methanol can be included as a preferable alcohol solvent.

The ratio of water and the organic solvent is typically 90:10 to 0.01:99.99 by weight ratio, and it is preferably 50:50 to 0.01:99.99. When the ratio of water becomes too large, there is the case that an epoxy compound reacts with water to be ring-opened and deteriorated, therefore the selectivity ratio of the epoxy compound lowers.

On the contrary, when the ratio of the organic solvent becomes too large, cost for recovering the solvent increases and therefore the ratio mentioned above is adopted.

In the method of the present invention, a method of adding an ammonium salt to the reaction solvent with a titanosilicate and a quinoid compound is effective because the method enables to prevent the catalyst activity from being decreased or further enhance the catalyst activity and/or increase use efficiency of hydrogen. The ammonium salt may be used with a noble metal or may be respectively used independently. The addition amount of the ammonium salt is typically 0.001 mmol/kg to 100 mmol/kg per unit weight of the solvent (per the weight of water and an organic solvent in total).

Examples of the ammonium salt include salts comprising (1) an anion selected from a sulfate ion, a hydrogen sulfate ion, a carbonate ion, a hydrogen carbonate ion, a phosphate ion, a hydrogen phosphate ion, a dihydrogen phosphate ion, a hydrogen pyrophosphate ion, a pyrophosphate ion, a halogen ion, a nitric acid ion, a hydroxide ion or C1-C10 carboxylic acid ions and (2) a cation selected from an ammonium, an alkyl ammonium, an alkylaryl ammonium.

Examples of the $C_1$-$C_{10}$ carboxylic acid ion include an acetic acid ion, a formic acid ion, an acetic acid ion, a propionic acid ion, a butyric acid ion, a valeric acid ion, a caproic acid ion, a caprylic acid ion and a capric acid ion.

Examples of alkyl ammonium include tetramethylammonium, tetraethylammonium, tetra-n-propylammonium, tetra-n-butylammonium and cetyltrimethylammonium. Examples of alkali metal or alkaline-earth metal cations include a lithium cation, a sodium cation, a potassium cation, a rubidium cation, a cesium cation, a magnesium cation, a calcium cation, a strontium cation and a barium cation.

Examples of preferable ammonium salts include ammonium salts of an inorganic acid such as ammonium sulfate, ammonium hydrogen sulfate, ammonium carbonate, ammonium hydrogen carbonate, diammonium hydrogen phosphate, dihydrogen phosphate ammonium, ammonium phosphate, hydrogen pyrophosphate ammonium, pyrophosphate ammonium, ammonium chloride and ammonium nitrate or ammonium salts of a $C_1$-$C_{10}$ carboxylic acid such as ammonium acetate. Examples of more preferable ammonium salts include dihydrogen phosphate ammonium.

The olefin usable in the present invention means a hydrocarbon having one or more carbon-carbon double bond. Examples of the olefin used in the present invention include aliphatic olefins such as ethylene, propylene, 1-butene, 2-butene, 1-pentene, 1-hexene and 2-hexene, cyclic olefins such as cyclopentene and cyclohexene, diolefins such as butadiene, and olefins having an aromatic ring such as styrene.

The present invention is preferably used in a method for producing an epoxide from a $C_2$-$C_6$ olefin such as ethylene, propylene, 1-butene, 2-butene, 1-pentene, 1-hexene, 2-hexene, cyclopentene, cyclohexene and butadiene and can be particularly preferably used in a method for producing propylene oxide from propylene.

Examples of the reaction method of the reaction by the present invention include a fixed bed flow reaction method or a flow type complete mixing slurry reaction method.

The partial pressure ratio of oxygen and hydrogen to supply to the reaction vessel is typically in the range of 1:50 to 50:1. The partial pressure ratio of oxygen and hydrogen is preferably 1:2 to 10:1. When the partial pressure ratio of oxygen and hydrogen (oxygen/hydrogen) is too high, there is a case that generation rate of epoxide lowers. In the meantime, when the partial pressure ratio of oxygen and hydrogen (oxygen/hydrogen) is too low, there is a case that the selectivity of the epoxy compound decreases due to the increase in the paraffin by-production. Oxygen and hydrogen gas usable in this reaction can be diluted with a gas for dilution and subjected to the reaction. As a gas for dilution, nitrogen, argon, carbon dioxide, methane, ethane and propane can be included. The concentration of the gas for dilution is not limited in particular but oxygen or hydrogen is diluted as needed and used.

An oxygen gas or air can be included as oxygen material. As an oxygen gas, an oxygen gas produced by inexpensive pressure swing method can be used and a high purity oxygen gas produced by low temperature separation can be used as required.

The reaction temperature in this reaction is typically 0° C. to 150° C., and preferably 40° C. to 90° C. When the reaction temperature is too low, reaction rate becomes slow, and when the reaction temperature becomes too high, by-product by side reaction increases.

The reaction pressure is not limited in particular but it is typically 0.1 MPa to 20 MPa in gauge pressure, and preferably 1 MPa to 10 MPa. When the reaction pressure is too low, dissolution of the raw material gas becomes insufficient and the reaction rate becomes slow. When reaction pressure is too high, costs of the apparatus involved in the reaction increase.

Collection of the epoxy compound which is the product of the present invention can be performed by normal distillation separation.

EXAMPLES

The present invention will now be explained with reference to examples, but the present invention is not limited to these Examples.

Example 1

TS-1 which was used in this reaction was prepared by the method described in Journal of Catalysis 130, (1991), 1-8. It was confirmed by measuring X-ray diffraction pattern that the resultant powder had a TS-1 structure and the titanium content by ICP optical emission spectrometry was 1.3% by weight.

Catalyst A

Similarly, the Pd/carbon black (CB) catalyst used in this reaction was prepared following the method described in US Patent Application Publication No. 2005-0014636. 500 mL of an aqueous solution containing 0.56 mmol of palladium chloride, 0.006 mmol of platinum chloride, sodium polyacrylate (molecular weight: 1200, 1.27 mmol) and 30 mmol of hydrogen chloride was mixed in a 500 mL eggplant flask, and stirred at room temperature under air atmosphere for one hour. Hydrogen gas was introduced into this mixture at a rate of 100 ml/min at room temperature for 20 minutes to form a Pd colloid. To the colloidal solution mentioned above, 6 g of commercially available CB (SEAST 9, produced by Tokai Carbon Co., Ltd.) and the mixture was stirred for eight hours. After the stirring was ended, water was removed using a rotary evaporator and was further dried under vacuum at 50° C. for 12 hours. The resultant catalyst precursor powder was calcined under nitrogen atmosphere at 300° C. for six hours to obtain a Pd/CB catalyst. The palladium content by ICP optical emission spectrometry was 1.01% by weight and the platinum content was 0.02% by weight.

In the reaction, an autoclave having a volume of 0.5 L was used as a reaction vessel and to this were supplied raw material gas having a volume ratio of propylene/oxygen/hydrogen/nitrogen of 4/3/8/85 at a rate of 16 L/hour and a solution of water/methanol=20/80 (weight ratio) containing 0.7 mmol/kg of anthraquinone at a rate of 108 mL/hour and the liquid phase of the reaction mixture was taken out of the reaction vessel through a filter, thereby performing a continuous reaction under the conditions of a temperature of 60° C., a pressure of 0.8 MPa (gauge pressure) and a residence time of 90 minutes. During this period, 131 g of reaction solvent, 0.133 g of TS-1, and 0.03 g of Pd/CB were allowed to be present in the reaction mixture in the reaction vessel.

The liquid phase and the gaseous phase were taken out after 5 hours from the start of the reaction and analyzed by gas chromatography, and the results showed that the propylene oxide generation activity per unit weight of TS-1 was 6.32 mmol-PO/g-TS-1·h and the selectivity based on propylene was 88%.

Comparative Example 1

The same operation as in Example 1 was performed except that a solution of water/methanol=20/80 containing no additives was used in place of a solution of water/methanol=20/80 containing 0.7 mmol/kg of anthraquinone. The liquid phase and the gaseous phase were taken out after 5 hours from the start of the reaction and analyzed by gas chromatography, and the results showed that the propylene oxide generation activity per unit weight of TS-1 was 6.45 mmol-PO/g-TS-1·h and the selectivity based on propylene was 27%.

Comparative Example 2

The same operation as in Example 1 was performed except that an aqueous solution containing 545 mmol/kg of hydroquinone was used in place of a solution of water/methanol=20/80 containing 0.7 mmol/kg of anthraquinone. The liquid phase and the gaseous phase were taken out after 5 hours from the start of the reaction and analyzed by gas chromatography, and the results showed that the propylene oxide generation activity per unit weight of TS-1 was 0.15 mmol-PO/g-TS-1·h and the selectivity based on propylene was 48%.

TABLE 1

| Example/ Comparative Example | Pd Catalyst | Additive Amount (mmol/kg) | Solvent | Activity mmol-PO/g- TS-1 · h | PO selectivity (based on propylene) % | PO generation rate mmol/h | Propane generation rate mmol/h |
|---|---|---|---|---|---|---|---|
| Example 1 | A | Anthraquinone (0.7 mmol/kg) | Methanol/water (4/1 weight) | 6.32 | 88 | 0.84 | 0.11 |
| Comparative Example 1 | A | None | Methanol/water (4/1 weight) | 6.45 | 27 | 0.86 | 2.29 |
| Comparative Example 2 | A | Hydroquinone (545 mmol/kg) | Water | 0.15 | 48 | 0.02 | 0.02 |

INDUSTRIAL APPLICABILITY

The present invention provides a method for more effectively producing an epoxy compound from an olefin, oxygen and hydrogen.

The invention claimed is:

1. A method for producing an epoxy compound, comprising contacting an olefin, oxygen and hydrogen with a noble metal and a crystalline titanosilicate having an MFI structure in a liquid phase in the presence of a quinoid compound represented by Formula (2)

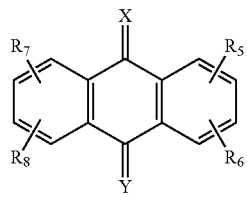

wherein X and Y, which are the same or different, represent an oxygen atom or an NH group; and $R_5$, $R_6$, $R_7$ and $R_8$, which are the same or different, represent a hydrogen atom, a hydroxyl group or an alkyl group, or a dihydro compound thereof.

2. The production method according to claim 1, wherein the crystalline titanosilicate having an MFI structure is TS-1.

3. The production method according to claim 1, wherein the noble metal is palladium, platinum, ruthenium, rhodium, iridium, osmium, gold or an alloy or a mixture thereof.

4. The production method according to claim 3, wherein the noble metal is palladium.

5. The production method according to claim 1, wherein the olefin is a $C_2$-$C_6$ olefin.

6. The production method according to claim 5, wherein the olefin is propylene.

7. The production method according to claim 1, wherein the liquid phase comprises water, an organic solvent or a mixture thereof, and said organic solvent comprises at least one organic solvent selected from group consisting of alcohol, ketone, nitrile, ether, aliphatic hydrocarbon, aromatic hydrocarbon, halogenated hydrocarbon, ester, and glycol.

8. The production method according to claim 7 wherein the organic solvent is alcohol.

9. The production method according to claim 7, wherein the alcohol is methanol.

10. The production method according to claim 7, wherein the water or the mixture of water and an organic solvent further contains an ammonium salt.

11. The production method according to claim 10, wherein the ammonium salt is a salt comprising (1) an anion selected from a sulfate ion, a hydrogen sulfate ion, a carbonate ion, a hydrogen carbonate ion, a phosphate ion, a hydrogen phosphate ion, a dihydrogen phosphate ion, a hydrogen pyrophosphate ion, a pyrophosphate ion, a halogen ion, a nitric acid ion, a hydroxide ion and $C_1$-$C_{10}$ carboxylic acid ions, and (2) a cation selected from the group consisting of an ammonium, an alkyl ammonium, and an alkylaryl ammonium cation.

12. The production method according to claim 10, wherein the ammonium salt is an ammonium dihydrogen phosphate.

* * * * *